United States Patent
Balducci et al.

(10) Patent No.: US 6,337,296 B1
(45) Date of Patent: Jan. 8, 2002

(54) PROCESS FOR THE PREPARATION OF CATALYSTS BASED ON MFI-TYPE ZEOLITE

(75) Inventors: Luigi Balducci, Mortara; Roberto Buzzoni, San Mauro Torinese; Leonardo Dalloro, Bollate; Giordano De Alberti, Besnate, all of (IT)

(73) Assignee: Enichem S.p.A., San Donato Milanese (IT)

( * ) Notice: Subject to any disclaimer, the term of this patent is extended or adjusted under 35 U.S.C. 154(b) by 0 days.

(21) Appl. No.: 09/429,904

(22) Filed: Oct. 29, 1999

(30) Foreign Application Priority Data

Nov. 6, 1998 (IT) .......................................... MI98A2416

(51) Int. Cl.[7] ................................................ B01J 29/00
(52) U.S. Cl. .............................. 502/64; 502/63; 502/71; 502/77
(58) Field of Search .............................. 502/63, 64, 71, 502/77

(56) References Cited

U.S. PATENT DOCUMENTS

| 4,126,579 | A |   | 11/1978 | Flaherty et al. |
| 4,359,421 | A |   | 11/1982 | Bell et al. |
| 4,826,793 | A | * | 5/1989  | Velten et al. |
| 5,731,261 | A | * | 3/1998  | Balducci et al. |
| 5,849,258 | A | * | 12/1998 | Lujano et al. |
| 5,914,398 | A | * | 6/1999  | Carati et al. |
| 6,106,803 | A | * | 8/2000  | Hasenzahl et al. |

FOREIGN PATENT DOCUMENTS

| EP | 0 380 364 | 8/1990 |
| EP | 0 791 558 | 8/1997 |

* cited by examiner

Primary Examiner—Steven P. Griffin
Assistant Examiner—Christina Ildebrando
(74) Attorney, Agent, or Firm—Oblon, Spivak, McClelland, Maier & Neustadt, P.C.

(57) ABSTRACT

The present invention relates to a process for the preparation of catalysts suitable for the transposition reaction of oximes to amides. The process consists in englobing submicronic particles of MFI-type zeolites in a siliceous ligand substantially inactive in the above reactions.

11 Claims, No Drawings

PROCESS FOR THE PREPARATION OF CATALYSTS BASED ON MFI-TYPE ZEOLITE

The present invention relates to a process for the preparation of catalysts based on MFI-type zeolite prepared in spheroidal form and active in transposition reactions of oximes to amides.

More specifically, the present invention relates to a process for the preparation of catalysts based on MFI-type zeolites, suitable for use in gas phase in fluid-bed and entrained-bed reactors.

The invention also relates to catalysts obtained by the above processes.

Zeolites of the MFI type, in particular those with a high silica/alumina ratio (U.S. Pat. No. 4,359,421) and, more generally, those with a low content of trivalent heteroelements (patent EP 242.960), are known in literature as basic material for the preparation of catalysts which can be used in the transposition reaction of oximes to amides.

Among these reactions, those carried out in gas phase which use solids based on zeolites are of particular importance. For example, the patent EP 234.088 describes a method for the preparation of ε-caprolactam which consists in putting cyclohexanonoxime, in gaseous state, in contact with crystalline alumino-silicates having well-defined physico-chemical characteristics and preformed in the form of granules (24–48 mesh).

Although they consist of active component alone, these materials have limited possibilities of being used in industrial reactors; in fact, if fluid-bed or entrained-bed reactors are used for the catalytic process, the catalysts should preferably be in the form of microspheres, with an average diameter of 30–100 μm and characterized by a high resistance to interparticle attrition and attrition against the walls of the reactors; if, on the other hand, fixed-bed reactors are used, the catalysts should have the typical forms for this technology (speres, tablets, etc.) with dimensions of approximately a few millimeters and characterized by a good mechanical stress resistance.

The cohesion between the individual and submicronic particles of the microcrystalline zeolitic material is generally poor and consequently resistance to attrition and mechanical stress is normally obtained by combining the zeolitic material with compounds of an inorganic nature (ligands) in forming phase.

Catalysts based on zeolites, suitable for use in fluid-bed or entrained-bed reactors and with the characteristics listed above, are widely described in the known art and are mainly used in catalytic cracking processes (FCC catalysts, Fluid Catalytic Cracking).

The forming of the above catalysts, when microspheres with a diameter <100 μm are required, is usually carried out with the well-known spray-drying technique.

Silicas and aluminum oxides in the colloidal state or silico-aluminates are used as ligands to give the microspheres a higher mechanical resistance to attrition; the quantities of the above ligands in the resulting catalytic compositions is normally less than 30% by weight.

The use of siliceous ligands in spherulization processes of MFI-type zeolitic materials suitable for the transposition reaction of oximes to amides, however, is not widely used as amorphous silica is not completely inactive in the above reactions.

It is known in fact that this compound may significantly jeopardize the selectivity of the zeolitic catalyst and deteriorate the catalytic performance due to the formation of organic pitches.

It has been observed, for example, that silica gels characterized by the presence of hydroxylic groups with a low acidity, have a high activity, low selectivity and rapid formation of pitch in transposition reactions of cyclohexanonoxime to ε-caprolactam [Catalysis Letters 17 (1993), 139–140; Catalysis Today 38 (1997), 249–253].

To overcome this problem patent EP 576.295 suggests, for example, preforming the zeolitic material in a spherical form by spray-drying without any addition of ligands and subjecting the microspheres, in a subsequent process phase, to thermal treatment in water to increase their hardness.

A process has now been found for the preparation of catalysts based on zeolitic materials and siliceous ligands, suitable for use in reactions of oximes to amides, which overcomes the drawbacks of the known art.

In particular, the present invention relates to a process for the preparation of catalysts based on MFI-type zeolitic compounds and siliceous ligands characterized in that submicronic particles of zeolite are incorporated into a ligand obtained by the acid hydrolysis of silicon alkoxide.

The innovative aspect of the invention basically consists in the use of oligomeric species of silica synthesized in an acid medium as ligands of MFI-type zeolitic materials.

The catalysts obtained by the process of the invention have a high resistance to attrition and mechanical stress and an excellent catalytic activity.

In particular, the siliceous ligands used, consisting of oligomeric species of silica synthesized by the acid hydrolysis of silicon alkoxides, overcome the disadvantages deriving from their use in the transposition reaction of oximes to amides, because they do not interact in the reaction itself.

This behaviour is in distinct contrast with that of catalysts containing ligands prepared in an alkaline medium, as described, for example, in U.S. Pat. No. 4,859,785 (hydrolysis of silicon alkoxides with organic bases), or basic solutions of colloidal silicons, known commercially under the trade-name of "Ludox".

It has also been found that the ligands used in the process of the invention can also be advantageously used in the known forming operations of zeolitic materials into spherical form.

In particular, the ligands of the invention have been used in emulsifying/gelation techniques, which consist in dispersing the submicronic particles of zeolitic material in the acid solution of the siliceous ligand and subjecting the resulting mixture to emulsification and gelation in an organic medium.

With this technique, catalytic compositions are obtained in spherical form and with morphological-granulometric, physico-chemical characteristics and resistance to attrition suitable for use in the transposition reactions of oximes to amides in fluid-bed or entrained-bed reactors.

In particular, the catalytic compositions based on MFI-type zeolite which are obtained, consist of microspheres with an average diameter varying from 20 to 200 μm and are characterized by a content of siliceous ligand (expressed as $SiO_2$) equal to or higher than 30% by weight, an external surface area (A.S.E.) varying from 60 to 80 $m^2/g$, a specific volume of the micro and mesopores varying from 0.2 to 0.3 ml/g and 0.1 to 0.4 ml/g respectively, bulk density values ranging from 0.7 to 0.85 g/ml and resistance to attrition, expressed as D.I. (Davison Index) less than or equal to 6.

The above catalysts significantly differ from those known in the art in their high content of siliceous ligand ($\geq 30\%$), thus confirming the low catalytic activity of the ligand in transposition reactions of oximes to amides.

A further object of the invention consists of a process for the catalytic transposition of oximes to amides characterized in that the reaction is carried out in the presence of the catalysts of the invention.

In particular, the catalysts obtained by the emulsification/gelation technique have morphological-granulometric, physico-chemical characteristics and resistance to attrition suitable for use in transposition reactions of oximes to amides in fluid-bed or entrained-bed reactors.

The emulsification/gelation technique used for forming the catalysts of the present invention comprises in particular the following steps:

preparation of siliceous oligomers by the hydrolysis of silicon alkoxides;

mixing said oligomers with an aqueous or hydroalcohol dispersion of submicronic particles of MFI-type zeolite acidified to pH≦5;

spherulization of the resulting mixture.

In the preparation of the siliceous oligomers, silicon alkoxides are used as silica precursors, such as for example tetra-ethyl-orthosilicate (TEOS). The hydrolysis of these compounds in an aqueous medium catalyzed by acids, as well as the effect of the hydrolysis conditions on the physico-chemical characteristics of the siliceous oligomers, are widely described in the art [C. J. Brinker, G. W. Shere "Sol-Gel Science. The Physic and Chemistry of sol-gel processing", Academic Press Inc., 1990].

Siliceous oligomers suitable for the purposes of the present invention are preferably obtained by the hydrolysis of TEOS in an aqueous medium and in the presence of mineral acids, such as for example, HCl and $HNO_3$, regulating the molar ratio $H_2O$/TEOS between 10 and 25 and the pH between 1.5 and 3.0. The hydrolysis reaction is carried out maintaining the reagents (TEOS and acid aqueous solution) under mechanical stirring for times varying from 1 to 3 hours at temperatures generally between 20 and 40° C. The concentration of alcohol in the reaction mixture (in particular of ethanol deriving from the hydrolysis of TEOS) may be appropriately corrected in a subsequent operation depending on the technology adopted in the spherulization of the zeolitic material. For example the solution of siliceous oligomers may be dealcoholated and concentrated by distillation at reduced pressure and at a temperature of less than 30° C., or it may be further diluted with alcohol or with hydro-alcohol solutions.

The MFI-type zeolitic compounds suitable for the transposition reaction of oximes to amides can be selected from Silicalite-1 or zeolites with a low content of aluminum (molar ratio Si/Al>1000) or other trivalent or tetravalent heteroatoms, such as those of Group III (B, Ga, In) or Ti.

As described in the known art, these materials are obtained by hydrothermal synthesis from a mixture of reagents comprising a precursor of silica with a high purity (for example TEOS), water, alcohols, organic amines or cations of tetra-alkyl-ammonium ($RnN^+$) as agents for controlling the crystallization (templating agents) of the zeolitic material.

The reaction product, consisting of individual microcrystalline particles, normally having dimensions of less than 1 $\mu$m, is generally separated from the mother liquor by centrifugation, is then repeatedly washed with water to remove the excess templating agent and finally dried and calcined. Alternatively the reaction product can be spray-dried.

In the process for the prepration of the catalysts of the present invention the zeolitic intermediate is advantageously centrifuged and washed with water. This intermediate, in a thickened form, is dispersed in an aqueous or hydro-alcohol medium using mechanical dispersers or also ultrasonic devices and the dispersion conditions are checked to ensure that the dimensions of the material reach values close to those of the individual particles (normally less than 1 $\mu$m). The control of the dispersion degree of the zeolitic material in the aqueous medium is particularly important when dried zeolitic intermediates, and mainly zeolitic materials subjected to thermal treatment at a temperature of ≧500° C., are used in the process.

Under the preferred conditions, when a zeolitic intermediate which has been centrifuged and optionally washed, is used, the pH of the resulting aqueous or hydro-alcohol solution is normally alkaline owing to the incomplete removal of the templating agent. To avoid the formation of undesired polymerization or gelation phenomena of the acid siliceous oligomers in the subsequent mixing operation, the above dispersions are acidified up to pH values less than or equal to 5.0. This operation, which does not usually appear in the description of processes for the preparation of zeolitic materials, is therefore a fundamental point of the present invention.

The acidification can be carried out with solutions of mineral or organic acids and, under the preferred conditions, with the type of acid used in the preparation of the siliceous ligand, such as for example HCl and $HNO_3$. The quantity of acid is controlled so that the pH of the resulting ligand/zeolite mixture is less than 4.0, preferably between 2.0 and 3.0 inclusive.

With respect to the composition of the above mixture, the weight ratio between the MFI-type zeolitic compound and the siliceous ligand (expressed as $SiO_2$) can be extended up to values of 2.5 inclusive, thus obtaining catalytic compositions in which the siliceous ligand is contained in a quantity of up to 50% by weight; under the preferred conditions the siliceous ligand is between 30 and 50% by weight.

The concentration of the solid (MFI-type zeolite) in the aqueous or hydro-alcohol solution of the siliceous ligand is established each time in relation to the technology adopted to obtain materials in spherical form, such as for example, spray-drying or emulsification/gelation in organic media.

In particular the spherulization process followed to illustrate the invention consists in emulsifying the aqueous or hydro-alcohol ligand/zeolite mixture in an organic medium (decanol) and consolidating the microdrops of dispersed phase by rapidly bringing the emulsion in contact with a basic solution (solution of cyclohexylamine in decanol). The microspheres of gel thus obtained are subsequently separated from the basic solution, washed repeatedly with ethanol, dried and finally calcined in an oxidating atmosphere (air) at a temperature of over 450° C. and, normally, within the typical temperature range of zeolitic materials (500–550° C.) with a heating rate generally of about 50° C./h.

The materials prepared with the above process consist of microspheres whose dimensions can vary from 20 to 200 $\mu$m depending on the emulsifying conditions of the ligand/zeolite mixture. These materials, owing to their morphological-granulometric and physico-chemical characteristics described above, can be conveniently used in processes for the preparation in gas phase of amides by the catalytic transposition of oximes.

Among amides, which form an important group of intermediates, caprolactam is considerably important, in particular for the preparation of polyamidic resins and synthetic fibres.

This compound is at present produced industrially by transposition in liquid phase with sulfuric acid or oleum, a technology that has numerous problems linked to the use of sulfuric acid.

The necessity for an alternative process for the preparation of caprolactam such as that of the present invention was therefore particularly felt.

In particular, the catalysts of the present invention can be advantageously used in the transposition reaction of cyclohexanonoxime to ε-caprolactam with a process in gas phase, consisting in bringing cyclohexanonoxime vapours in contact with the catalyst.

This reaction can be carried out at a pressure ranging from 0.05 to 10 bars and at a temperature ranging from 250 to 500° C., preferably from 300 to 450° C.

More specifically, the cyclohexanonoxime is fed to a reactor containing the catalyst, in vapour phase and in the presence of one or more solvents and, optionally, also an uncondensable gas. Under the preferred conditions the cyclohexanonoxime is dissolved in a mixture of solvents, described below, at a concentration ranging from 5 to 25% by weight and preferably between 6 and 15%; the solution thus obtained is then vaporized and fed to the reactor.

Preferred solvents are of the type $R_1$—O—$R_2$ wherein $R_1$ is a $C_1$–$C_4$ alkyl chain and $R_2$ can be a hydrogen atom or an alkyl chain containing a number of carbon atoms less than or equal to $R_1$. Alcohols with a $C_1$–$C_2$ alkyl chain are particularly preferred. These solvents can be used alone or mixed with each other, or combined with an aromatic hydrocarbon such as benzene or toluene.

The feeding rate of the cyclohexanonoxime is checked so that the WHSV value (Weight Hourly Space Velocity), expressed as kg of cyclohexanonoxime/kg of catalyst/h, is between 0.1 and 50 $h^{-1}$, preferably between 0.5 and 20 $h^{-1}$.

During the transposition reaction of cyclohexanonoxime to ε-caprolactam, the catalytic performance undergoes deterioration due to the formation of organic pitches which obstruct the pores of the catalyst and poison its active centres. The deterioration process is slow and depends on the operating conditions and, in particular, the WHSV, type of solvents, feeding composition, temperature and pressure. The catalytic activity however can be effectively re-integrated by combustion of the pitches, oxidating treatment in a stream of air, optionally diluted with nitrogen, at a temperature ranging from 450 to 550° C., preferably between 450 and 500° C.

The presence of silica in the catalytic composition does not substantially jeopardize the catalytic performance of the zeolitic material (active component). In fact, if the reaction is carried out under identical WHSV conditions (referring to the weight of active component in the catalyst), the conversion yield of cyclohexanonoxime and, above all, the selectivity to ε-caprolactam are in line with those of the catalyst consisting of active component alone. Also the pitching rate does not undergo variations; the deterioration in the performance therefore remains unaltered and it is not necessary to increase the frequency of the regenerations.

Some illustrative but non-limiting examples are provided for a better illustration of the present invention and for its embodiment.

EXAMPLE 1
Preparation of Silicalite-1

632 g of aqueous solution at 20% of Tetra-propyl-ammonium-hydroxide (TPAOH) are charged into a 3 liter pyrex reactor, flushing with nitrogen. 555 g of tetra-ethyl-orthosilicate (TEOS) are added dropwise in about 5 hours, stirring and flushing with nitrogen. The day after the solution is closed in a 5 liter autoclave inside a teflon container. Three loading-discharging sequences of about 10 atm of nitrogen are effected. Hydrothermal synthesis is then carried out at 140° C. for 24 hours with stirring of 80 revs/minute.

The solid dried by spray-drying is separated on part of the suspension. The suspension, coming from the synthesis, containing the zeolite is fed to the spray-drying at a rate of 1.5 liters/hour, and an inlet temperature of 230° C. The solid recovered is kept dry without undergoing further treatment.

Another aliquot of suspension is centrifuged, separating the solid product which is washed with distilled water until the washing water reaches pH≈7. The product obtained is maintained humid and is spherulized as described in the following examples.

Part of the centrifuged solid is dried at 120° C., calcined at 550° C. for 4 h and subsequently sieved at a size of 42÷80 meshes for the catalytic activity test (Example 9).

X-ray diffraction of the calcined product identifies the product as MFI zeolite.

Chemical analysis carried out by ICP-AES shows low contents of Na, K, Al, Fe (<30 ppm).

Morphological analysis of the material, carried out by ASAP 2000 (isotherm absorption of nitrogen at 77 K), gave the results: A.S.E.=55.1 $m^2/g$, micropore volume=0.183 $cm^3/g$, mesopore volume=0.264 $cm^3/g$.

The bulk density of the catalyst, sieved at a size of 42÷80 mesh proved to be 0.63 $g/cm^3$.

EXAMPLE 2

Preparation of a Microspheriodal Catalyst Consisting of Silicalite-1 and Silica A description follows of the preparation of a Silicalite-1

Silica composite material containing 50% by weight of Silicalite-1.

A. Preparation of the solution: 213 g of TEOS (Aldrich; titer 98%), 288 g of demineralized water and 3.0 g of HCl 1N are charged into a cylindrical reactor having a capacity of 1000 $cm^3$ equipped with a mechanical stirrer, thermometer and external cooling bath. The reagents are maintained under stirring at a temperature of 25–30° C. for the time necessary to obtain a limpid solution (about 35 minutes); the stirring is then continued for a further 60 minutes. The acid silica sol thus obtained (pH=2.5; Titer $SiO_2$=11.9%) is conserved in a frigerator at 5° C. until the moment of use.

B. The washed and thickened product, as described in Example 1 (titer of Silicalite-1=59.6%) is used as Silicalite precursor. 9.58 g of the precursor (equal to 5.71 g of Silicalite-1) is dispersed for 60 minutes in 60 $cm^3$ of demineralized water using a magnetic stirrer with a teflon anchor and, subsequently, for a further 15 minutes with an ultrasonic probe (Sonifier, Cell Disruptor B15; Branson); after dilution with 60 $cm^3$ of ethanol the treatment is continued in ultrasounds for a further 10 minutes. The hydro-alcohol suspension of Silicalite-1, consisting of particles with an average diameter of 0.22 μm (Coulter Analyzer, Model N4, 5D), is subsequently acidified from pH≈10.5 to pH=2.5 with a solution of HCl 1N and is then mixed with 48 g of silica sol A) for about 3 minutes using a magnetic stirrer.

C. The mixture thus obtained (about 170 $cm^3$) is transferred to a cylindrical reactor (internal diameter 100 mm, volume 1000 $cm^3$) previously charged with 500 $cm^3$ of 1-decanol (Fluka, titer 98%); the mechanical stirrer with 6 radial blades is activated and the rate regulated to 800 revs per minute. After 10 minutes the emulsion is rapidly discharged from the bottom of the reactor into an underlying container containing 300 $cm^3$ of a solution at 10% (v/v) of cyclohexylamine (Aldrich, titer 99%) in 1-decanol, the mechanical stirring being maintained at room temperature. The stirring is continued for a further 60 minutes, the solid is then left to deposit, for about 60 minutes, and is subsequently filtered and washed repeatedly with ethanol. After drying at room temperature the composite material is calcined in an oxidating atmosphere (air) at 550° C. for 4 hours at a heating rate of 50° C./h.

The composite material thus obtained contains 50% by weight of Silicalite-1.

The average diameter (D50) of the microspheres, measured with a Coulter LS130 apparatus, is equal to 51 $\mu$m (<10% at 8 $\mu$m, <25% at 36 $\mu$m, <50% at 51 $\mu$m, <75% at 67 $\mu$m, <90% at 82 $\mu$m).

Morphological analysis of the material, carried out by ASAP 2000, gives the results: A.S.E.=62.7 $m^2$/g, micropore volume=0.301 $cm^3$/g, mesopore volume=0.102 $cm^3$/g.

The bulk density of the catalyst proves to be 0.83 $g/cm^3$.

The resistance to attrition of the catalyst of Example 2 was verified using the Davison Attrition Index method (D.I.) ["Advances in Fluid Catalytic Cracking" Catalytica, Mountain View, Calif., Part 1, 1987, page 355] and proved to be in line with the values of a fresh catalyst according to the specification of use in an FCC reactor (D.I.<8).

EXAMPLES 3–4
Preparation of Microspheroidal Catalysts Consisting of Silicalite-1 and Silica The preparation of the composite material is carried out under the same operating conditions described in Example 2, but the composition of the material is varied.

Table 1 indicates the compositions, dimensions of the microspheres obtained and the morphological characteristics.

EXAMPLE 5
Preparation of a Microspheroidal Catalyst Consisting of Silicalite-1 and Silica Example 2 is repeated but, in this case, the emulsifying rate is regulated to 300 revs/minute.

The material obtained has the following characteristics:

Composition=50% by weight of Silicalite-1

Median diameter (D50) of the microspheres=90 $\mu$m

A.S.E.=68.9 $m^2$/g, micropore volume=0.278 $cm^3$/g, mesopore volume=0.132 $cm^3$/g Bulk density=0.84 $g/cm^3$

EXAMPLE 6
Preparation of a Microspheroidal Catalyst Consisting of Silicalite-1 and Silica The preparation of the Silicalite-Silica composite catalyst described in Example 2 is repeated varying the emulsifying rate to 400 revs/minute.

The material obtained has the following characteristics:

Composition=50% by weight of Silicalite-1

Median diameter (D50) of the microspheres=59 $\mu$m

The bulk density of the catalyst proves to be 0.83 $g/cm^3$

EXAMPLES 7–8

Example 6 is repeated, but in this case the concentrations of the reagents are varied. The preparation conditions of the catalysts (quantity of single reagents and emulsifying conditions) and the characteristics of the catalysts (compositions, microsphere dimensions and morphological characteristics) are indicated in Table 2.

EXAMPLE 9
Catalytic Activity Test of the Active Phase

The catalyst of Example 1 (sieved at a size of 42÷80 mesh) was tested in a tubular fixed-bed microreactor with the following characteristics: material=glass, length 200 mm, $\emptyset_{int}$=11.5 mm, sheath for thermocouple with $\emptyset_{ext}$=4 mm. The catalyst for the test (0.5 g) was diluted with granular quartz up to a volume of 2 $cm^3$; this charge was positioned in the reactor between two layers of quartz.

For an optimum catalytic performance, the CEOX is fed in a solution of three solvents: toluene, methanol and water. The solution of CEOX is preheated before being introduced into the reactor and is vaporized and mixed with nitrogen directly in the reactor before coming into contact with the catalyst.

In the activation phase of the activity test the catalyst is heated to the reaction temperature in a stream of nitrogen and dried for 1 hour; the mixture of solvents alone (toluene, methanol and water) is then fed for at least 30 minutes. The actual test begins when the solution of CEOX is sent onto the catalyst.

The mixture of effluent vapours from the reactor is condensed and samples are collected for evaluation of the catalytic performances. The samples are analyzed by gaschromatography and the catalytic performances are evaluated, calculating the conversion of CEOX and selectivity to CPL.

Table 3 indicates the operating conditions and catalytic performances at the 1st and 23rd test hour in the transposition reaction of CEOX to caprolactam (CPL).

EXAMPLES 10–16
Catalytic Activity Tests of Microspheroidal Catalysts Consisting of Silicalite-1 and Silica The catalysts described in examples 2-3-4-5-6-7-8 were tested as in Example 9. To respect the same WHSV, the different tests were carried out varying the catalyst charge and therefore also the contact time.

Table 4 indicates the catalytic performances at the 1st and 20th hour of the test.

EXAMPLE 17
Catalytic Activity Test with Fluid-bed of a Microspheroidal Catalyst Consisting of Silicalite-1 and Silica The catalyst described in Example 2 was tested in a fluid-bed reactor with the following characteristics: material=AISI 316 steel, length 500 mm, $\emptyset_{int}$=30 mm, sheath for thermocouple with $\emptyset_{ext}$=2 mm.

The activation procedure of the activity test is the same used for the tests in a fixed-bed reactor, but in this case the CEOX and solvents are preheated, vaporized and mixed with nitrogen before being introduced into the reactor.

The mixture of effluent vapours from the reactor is condensed and samples are collected for evaluation of the catalytic performances. The samples are analyzed by gaschromatography and the catalytic performances are evaluated calculating the conversion of CEOX and selectivity to CPL.

Table 5 indicates the operating conditions and catalytic performances at the 1st and 20th hour of the test.

EXAMPLES 18–20
Catalytic Activity Test with Fluid-bed of Microspheroidal Catalysts Consisting of Silicalite-1 and Silica The catalysts described in examples 3-4-5 were tested as in Example 17. To respect the same WHSV, the different tests were carried out varying the feeding flow-rate and contact time.

Table 6 indicates the catalytic performances at the 1st and 20th hour of the test.

Comparative Example 1
Preparation of a Microspheroidal Silica

A description follows of the preparation of a microspheroidal material based on silica sol.

170 cm³ of silica sol A) are emulsified in 500 cm³ of 1-decanol, regulating the stirring rate at 600 revs/minute. After 10 minutes the emulsion is discharged, from the bottom of the reactor, into a solution of cyclohexylamine at 10% (v/v) in 1-decanol. The same procedure described in Example 2 is then adopted.

The median diameter (D50) of the particles proved to be equal to 40 µm.

Comparative Example 2
Preparation of a Granular Catalyst Consisting of Silicalite-1 and Silica A description follows of the preparation of a Silicalite-1-Silica composite material containing 50% by weight of Silicalite-1.

46.1 g of anhydrous ethyl alcohol, 50 g of deionized water and 34 g of spray-dried silicalite (as described in Example 1) are charged into a 500 cm³ flask, stirring until complete dispersion (about 30 minutes). 1.30 g of a solution of HCl 3.5 M are then added to acidify up to a pH of about 2.5 together with a further 20.5 g of deionized water.

105 g of Tetra-ethyl-orthosilicate (TEOS) at 98% are added, the mixture is stirred and heated in a water-bath, in the presence of a reflux cooler, to 70–80° C. until a gel is formed. It is then heated for a further two hours at 70–80° C. The gel is left at room temperature for a night. The gel, compact and uniform, thus obtained is dried in a vacuum oven (pressure about 100 mm Hg) at 120° C. for a night.

The composite material is then calcined in an oxidating atmosphere (air) at 550° C. for 4 hours with a heating rate of 1° C./minute.

Before the catalytic test, the catalyst is ground and sieved; the 42÷80 fraction is used in the catalytic test.

Comparative Example 3
Preparation of a Granular Catalyst Consisting of Silicalite-1 and Silica A description follows of the preparation of a Silicalite-1-Silica composite material containing 50% by weight of Silicalite-1.

84.69 g of Tetra-propyl-ammonium-hydroxide (TPAOH) at 15% and 46.1 g of anhydrous ethyl alcohol are charged into a 500 cm³ flask and stirred for about 10 minutes. 34 g of spray-dried silicalite (as described in Example 1) are added, stirring until complete dispersion (about 30 minutes).

105 g of Tetra-ethyl-orthosilicate (TEOS) at 98% are added rapidly under stirring and there is complete gelation in a few minutes. The mixture is reflux heated using a water-bath to 70–80° C. for 2 hours approximately. The gel is left at room temperature for a night. The compact and uniform gel thus obtained is dried in a vacuum oven (pressure about 100 mm Hg) at 120° C. for a night.

The composite material is then calcined in an oxidating atmosphere (air) at 550° C. for 4 hours with a heating rate of 1° C./minute.

Before the catalytic test, the catalyst is ground and sieved; the 42÷80 fraction is used in the catalytic test.

Comparative Example 4
Preparation of a Granular Catalyst Consisting of Silicalite-1 and Silica A description follows of the preparation of a Silicalite-1-Silica composite material containing 50% by weight of Silicalite-1.

34 g of silicalite spray-dried as described above (corresponding to 30.2 g of $SiO_2$) and 88.8 g of LUDOX TMA silica ($SiO_2$=34%) are charged into a 300 cm³ beaker. The mixture is stirred for 30 minutes and is then dried on a plate at 150° C. The solid obtained is further dried in an oven at 120° C. for 12 h.

The composite material thus obtained is calcined in an oxidating atmosphere (air) at 550° C. for 4 hours with a heating rate of 1° C./minute.

Before the catalytic test, the catalyst is ground and sieved; the 42÷80 fraction is used in the catalytic test. The grinding and sieving procedure of the catalyst is obviously only useful for catalytic tests on a laboratory level but is not easily applicable on an industrial scale.

Comparative Example 5
Preparation of a Granular Catalyst Consisting of Silicalite-1 and Silica The same procedure is carried out as in comparative example 4, but using 75.5 g of Ludox AS40 ($SiO_2$= 40%).

Comparative Example 6
Preparation of a Granular Catalyst Consisting of Silicalite-1 and Silica The same procedure is carried out as in comparative example 4, but using 100.7 g of Ludox LS ($SiO_2$=30%).

Comparative Example 7
Catalytic Activity Test of Microspheroidal Silica

The catalyst described in comparative example 1 was tested as in Example 9, with a catalyst charge of 0.5 g.

Table 7 indicates the catalytic performances of this catalyst at the 1st and 3rd hour of the test.

The results show that silica synthesized in an acid environment has very little activity with respect to the active phase.

Comparative Examples 8–12
Catalytic Activity Tests of Granular Catalysts Consisting of Silicalite-1 and Silica The catalysts described in comparative examples 2-3-4-5-6 were tested as in Example 9, with a catalyst charge of 1.0 g.

Table 8 indicates the catalytic performances of this catalyst at the 1st and 20–24th hour of the test.

The results show that the composite catalyst prepared with silica synthesized in an acid environment has an improved selectivity with respect to that obtained with composite catalysts in which the silica has been prepared in another way.

TABLE 1

| Characteristics of the catalysts | | |
|---|---|---|
| Example | 3 | 4 |
| Silicalite-1 conc. (% w) | 60 | 70 |
| Diameter D50 (µm) | 60 | 57 |
| A.S.E. (m²/g) | 77.7 | 76.8 |
| V micro (cm³/g) | 0.225 | 0.206 |
| V meso (cm³/g) | 0.216 | 0.341 |
| Bulk Density (g/cm³) | 0.77 | 0.71 |

TABLE 2

| Example | 7 | 8 |
|---|---|---|
| Preparation conditions of the catalyst | | |
| Silicalite-1 precursor (g) | 8.46 | 12.70 |
| $H_2O$ (cm$^3$) | 40 | 40 |
| EtOH (cm$^3$) | 40 | 40 |
| Silica sol (g) | 48 | 72 |
| 1-DecOH (cm$^3$) | 400 | 430 |
| Emulsifying rate (rev/min) | 400 | 300 |
| Characteristics of the catalysts | | |
| Silicalite-1 conc. (% w) | 50 | 50 |
| Diameter D50 (μm) | 65 | 86 |
| Bulk Density (g/cm$^3$) | 0.77 | 0.71 |

TABLE 3

| Operating conditions | |
|---|---|
| Temperature | 350 |
| WHSV (h') (*) | 4.5 |
| Contact time (s) (#) | 0.11 |
| Partial pressure CEOX (bar) | 0.034 |
| MeOH/CEOX (molar) | 10 |
| Toluene/CEOX (molar) | 10 |
| $N_2$/CEOX (molar) | 8 |
| $H_2O$/CEOX (molar) | 0.15 |
| Catalyst charge (g) | 0.5 |

(*) The WHSV refers for the feeding only to CEOX and for the catalyst only to the active phase;
(#) The contact time refers to the total feeding mixture and to the composite catalyst.

| Catalytic performances | | |
|---|---|---|
| Time (h) | 1 | 23 |
| CEOX conversion (%) | 99.3 | 69.3 |
| Selectivity to CPL (%) | 93.5 | 95.5 |

TABLE 4

| Catalytic performances | | |
|---|---|---|
| Example | 10 | |
| Catalyst of example nr. | 2 | |
| Time (h) | 1 | 20 |
| CEOX conversion (%) | 100 | 89.8 |
| Selectivity to CPL (%) | 91.0 | 93.3 |
| Example | 11 | |
| Catalyst of example nr. | 3 | |
| Time (h) | 1 | 20 |
| CEOX conversion (%) | 99.9 | 93.9 |
| Selectivity to CPL (%) | 92.0 | 94.0 |
| Example | 12 | |
| Catalyst of example nr. | 4 | |
| Time (h) | 1 | 20 |
| CEOX conversion (%) | 99.7 | 84.7 |
| Selectivity to CPL (%) | 91.5 | 93.2 |
| Example | 13 | |
| Catalyst of example nr. | 5 | |
| Time (h) | 1 | 20 |
| CEOX conversion (%) | 99.7 | 81.4 |
| Selectivity to CPL (%) | 91.6 | 93.1 |
| Example | 14 | |
| Catalyst of example nr. | 6 | |
| Time (h) | 1 | 20 |
| CEOX conversion (%) | 99.9 | 90.0 |
| Selectivity to CPL (%) | 91.4 | 92.7 |
| Example | 15 | |
| Catalyst of example nr. | 7 | |
| Time (h) | 1 | 20 |
| CEOX conversion (%) | 99.7 | 84.0 |
| Selectivity to CPL (%) | 90.9 | 92.3 |

TABLE 4-continued

| Catalytic performances | | |
|---|---|---|
| Example | 16 | |
| Catalyst of example nr. | 8 | |
| Time (h) | 1 | 20 |
| CEOX conversion (%) | 99.9 | 83.3 |
| Selectivity to CPL (%) | 91.0 | 93.2 |

TABLE 5

| Operating conditions in fluid-bed microreactor | |
|---|---|
| Temperature | 350 |
| WHSV (h$^{-1}$) (*) | 3.8 |
| Contact time (s) (#) | 0.10 |
| Partial pressure CEOX (bar) | 0.035 |
| MeOH/CEOX (molar) | 10 |
| Toluene/CEOX (molar) | 10 |
| $N_2$/CEOX (molar) | 8 |
| $H_2O$/CEOX (molar) | 0.15 |
| Catalyst charge (g) | 3 |

(*) The WHSV refers for the feeding only to CEOX and for the catalyst only to the active phase;
(#) The contact time refers to the total feeding mixture and to the composite catalyst.

| Catalytic performances | | |
|---|---|---|
| Time (h) | 1 | 20 |
| CEOX conversion (%) | 95.3 | 83.0 |
| Selectivity to CPL (%) | 92.0 | 93.8 |

TABLE 6

| Catalytic performances | | |
|---|---|---|
| Example | 18 | |
| Catalyst of example nr. | 3 | |
| Time (h) | 1 | 20 |
| CEOX conversion (%) | 94.4 | 84.2 |
| Selectivity to CPL (%) | 94.2 | 94.5 |
| Example | 19 | |
| Catalyst of example nr. | 4 | |
| Time (h) | 1 | 20 |
| CEOX conversion (%) | 94.2 | 84.3 |
| Selectivity to CPL (%) | 93.2 | 94.3 |
| Example | 20 | |
| Catalyst of example nr. | 5 | |
| Time (h) | 1 | 20 |
| CEOX conversion (%) | 93.7 | 83.0 |
| Selectivity to CPL (%) | 90.0 | 93.9 |

TABLE 7

| Catalytic performances | | |
|---|---|---|
| Comparative example | 7 | |
| Catalyst of comparative example nr. | 1 | |
| Time (h) | 1 | 3 |
| CEOX conversion (%) | 0.5 | 0 |
| Selectivity to CPL (%) | 49.6 | — |

TABLE 8

| Catalytic performances | | |
|---|---|---|
| Comparative example | 8 | |
| Catalyst of comparative example nr. | 2 | |
| Time (h) | 1 | 20 |
| CEOX conversion (%) | 99.2 | 68.2 |

TABLE 8-continued

Catalytic performances

| | | |
|---|---|---|
| Selectivity to CPL (%) | 92.8 | 95.2 |
| Comparative example | 9 | |
| Catalyst of comparative example nr. | 3 | |
| Time (h) | 1 | 20 |
| CEOX conversion (%) | 99.8 | 69.4 |
| Selectivity to CPL (%) | 89.8 | 91.2 |
| Comparative example | 10 | |
| Catalyst of comparative example nr. | 4 | |
| Time (h) | 1 | 24 |
| CEOX conversion (%) | 99.7 | 36.6 |
| Selectivity to CPL (%) | 79.6 | 82.8 |
| Comparative example | 11 | |
| Catalyst of comparative example nr. | 5 | |
| Time (h) | 1 | 23 |
| CEOX conversion (%) | 99.4 | 28.5 |
| Selectivity to CPL (%) | 75.0 | 73.7 |
| Comparative example | 12 | |
| Catalyst of comparative example nr. | 6 | |
| Time (h) | 1 | 23 |
| CEOX conversion (%) | 99.9 | 15.0 |
| Selectivity to CPL (%) | 54.5 | 66.1 |

What is claimed is:

1. A process for the preparation of a catalyst suitable for the transposition reaction of an oxime to an amide, comprising:
   incorporating a submicronic particle of a MFI-type zeolitic compound into a siliceous ligand obtained by an acid hydrolysis of a silicon alkoxide;
   wherein the MFI-type zeolitic compound is selected from the group consisting of Silicalite-1 and a zeolite in which a molar ratio Si/Al or a molar ratio of Si to a hetero atom selected from the group consisting of B, Ga, In and Ti is >1000.

2. The process according to claim 1, wherein the catalyst is prepared by a spray drying method.

3. The process according to claim 1, wherein the catalyst is prepared in spherical form by dispersing said submicronic particle of the zeolitic compound in an acid solution of the siliceous ligand and subjecting a resulting mixture to emulsification and subsequently to gelation.

4. The process according to claim 3, further comprising the following steps:
   hydrolyzing said silicon alkoxide, thereby preparing a silicious oligomer;
   mixing said oligomer with an aqueous dispersion or hydroalcohol dispersion of said submicronic particle of the MFI-type zeolitic compound, thereby obtaining an aqueous mixture or hydroalcohol ligand/zeolite mixture;
   wherein said dispersion is acidified to pH≦5;
   spherulizing said aqueous mixture or hydroalcohol ligand/zeolite mixture by emulsion in an organic medium;
   contacting said emulsion with a basic solution, thereby consolidating microdrops of a dispersed phase;
   separating a microsphere of a gel;
   washing and calcinating of the microspheres of gel.

5. The process according to claim 4, wherein the siliceous oligomer is obtained by hydrolysis of TEOS in an aqueous medium and in the presence of a mineral acid;
   regulating a molar ratio $H_2O$/TEOS to between 10 and 25 and a pH to between 1.5 and 3.0; and
   maintaining said aqueous medium under mechanical stirring for 1 to 3 hours, at a temperature ranging from 20 to 40° C.

6. The process according to claim 5, wherein the mineral acid is HCl or $HNO_3$.

7. The process according to claim 4, wherein said aqueous dispersion or hydro-alcohol dispersion of the MFI-type zeolitic compound acidified to pH≦5 is prepared by dispersing the zeolitic compound in an aqueous medium or hydro-alcohol medium so that the dimensions of the zeolitic compound reach a value of less than 1 μm and acidifying the aqueous dispersion up to a pH value of less than or equal to 5.0.

8. The process according to claim 7, wherein the acidification of the aqueous dispersion is carried out with a mineral acid, if a mineral acid was used in the preparation of the siliceous ligand or an organic acid, if an organic acid was used in the preparation of the siliceous ligand so that the pH of a resulting ligand/zeolite mixture is less than 4.0.

9. The process according to claim 8, wherein the pH of the resulting ligand/zeolite mixture is between 2.0 and 3.0, inclusive 2.0 and 3.0.

10. The process according to claim 4, wherein the weight ratio between the MFI-type zeolitic compound and the siliceous oligomer, expressed as $SiO_2$ in the mixture, has a value of up to 2.5, inclusive of 2.5.

11. The process according to claim 1, wherein said siliceous ligand does not deteriorate the catalytic performance of said zeolitic compound in the transposition reaction of the oxime to the amide.

* * * * *